(12) United States Patent
Pénicaud

(10) Patent No.: US 9,381,471 B2
(45) Date of Patent: Jul. 5, 2016

(54) AEROGELS OF CARBON NANOTUBES

(75) Inventor: Alain Pénicaud, Bordeaux (FR)

(73) Assignee: Centre National de la Recherche Scientifique—CNRS, Paris (FR)

(*) Notice: Subject to any disclaimer, the term of this patent is extended or adjusted under 35 U.S.C. 154(b) by 676 days.

(21) Appl. No.: 12/743,969

(22) PCT Filed: Nov. 20, 2008

(86) PCT No.: PCT/FR2008/001627
§ 371 (c)(1),
(2), (4) Date: Jul. 6, 2010

(87) PCT Pub. No.: WO2009/101271
PCT Pub. Date: Aug. 20, 2009

(65) Prior Publication Data
US 2011/0124790 A1 May 26, 2011

(30) Foreign Application Priority Data

Nov. 21, 2007 (FR) ..................................... 07 08167

(51) Int. Cl.
| | |
|---|---|
| *B82Y 30/00* | (2011.01) |
| *B82Y 40/00* | (2011.01) |
| *C08K 3/04* | (2006.01) |
| *C08K 3/14* | (2006.01) |
| *B01D 71/02* | (2006.01) |
| *A61L 27/44* | (2006.01) |
| *B01J 21/18* | (2006.01) |
| *B01J 32/00* | (2006.01) |
| *C01B 31/02* | (2006.01) |
| *H01M 4/96* | (2006.01) |
| *H01G 11/34* | (2013.01) |
| *C02F 1/44* | (2006.01) |

(52) U.S. Cl.
CPC ............ *B01D 71/021* (2013.01); *A61L 27/443* (2013.01); *B01J 21/185* (2013.01); *B01J 32/00* (2013.01); *B82Y 30/00* (2013.01); *B82Y 40/00* (2013.01); *C01B 31/0273* (2013.01); *H01G 11/34* (2013.01); *H01M 4/96* (2013.01); *C01B 2202/02* (2013.01); *C01B 2202/06* (2013.01); *C02F 1/44* (2013.01); *Y02E 60/13* (2013.01); *Y02E 60/50* (2013.01)

(58) Field of Classification Search
CPC ... A61L 27/433; B01D 71/021; B01J 21/185; B01J 32/00; B82Y 30/00; B82Y 40/00; C01B 31/0273; H01G 11/34; H01G 11/3611
USPC .................. 524/495; 977/742, 842
See application file for complete search history.

(56) References Cited

U.S. PATENT DOCUMENTS

| | | | |
|---|---|---|---|
| 6,099,965 A | 8/2000 | Tennent et al. | |
| 6,684,524 B1 | 2/2004 | Sennhenn et al. | |
| 7,279,247 B2 | 10/2007 | Matarredona et al. | |
| 7,700,063 B2 | 4/2010 | Penicaud et al. | |
| 8,591,857 B2 | 11/2013 | Backov et al. | |
| 2003/0012722 A1* | 1/2003 | Liu ........................... | 423/447.3 |
| 2003/0092342 A1 | 5/2003 | Tennent et al. | |

FOREIGN PATENT DOCUMENTS

| | | |
|---|---|---|
| FR | 2 910 458 A | 6/2008 |
| JP | 2000-511864 A | 9/2000 |
| JP | 2007-161521 A | 6/2007 |
| JP | 2007-516925 A | 6/2007 |
| JP | 2007/517760 A | 7/2007 |
| JP | 2010-513202 A | 4/2010 |
| WO | WO 2005/069765 A2 | 8/2005 |
| WO | WO 2005/073127 A2 | 8/2005 |
| WO | WO 2008/096065 A1 | 8/2008 |

OTHER PUBLICATIONS

Bryning Mateusz B, et al, "Carbon Nanotube Aerogels", Advanced Materials, Mar. 5, 2007; pp. 661-664, vol. 19, No. 5, 2007 Wiley-VCH Verlag GmbH & Co. KGaA, Weinheim.
Chen, Jian, et al, "A new method for the preparation of stable carbon nanotube organogels", Carbon, Sep. 1, 2006, vol. 44, No. 11, Elsevier, Oxford, GB.
Penicaud A et al, "Dissolution Douce of Single Walled Carbon Nanotubes", AIP Conference Procedings AIP USA, 2005, pp. 266-270, No. 786, American Institute of Physics.
Sabba Y et al, "High-Concentration Dispersion of Single-Wall Carbon Nanotubes", Macromolecules 2004, Jun. 29, 2004, pp. 4815-4820, vol. 37, No. 13, American Chemical Society.
Hough L. A., et al, "Viscoelasticity of Single Wall Carbon Nanotube Suspensions", Physical Review Letters, Oct. 15, 2004, pp. 168102/1-4, vol. 93, No. 16, The American Physical Society.

* cited by examiner

*Primary Examiner* — Fred M Teskin
*Assistant Examiner* — Marie Reddick
(74) *Attorney, Agent, or Firm* — Arent Fox LLP

(57) ABSTRACT

The invention relates to a method for preparing aerogels of individualized carbon nanotubes and to the applications thereof, in particular in the production of composite aerogels and electrochemical compounds. The method of the invention is characterized in that it comprises the following steps carried out in an inert atmosphere: (a) reducing the carbon nanotubes using an alkaline metal in order to obtain a polyelectrolyte salt of carbon nanotubes; (b) exposing said polyelectrolyte salt of carbon nanotubes to an aprotic polar solvent in order to obtain a solution of individualized, reduced carbon nanotubes; (c) freezing said solution of individualized nanotubes; and (d) sublimating the solvent. The invention particularly relates to aerogels of individualized carbon nanotubes obtained by said method, and to the uses of said aerogels.

12 Claims, 4 Drawing Sheets

AEROGELS OF CARBON NANOTUBES

CROSS-REFERENCE TO RELATED APPLICATION

This application is a National Stage entry of International Application No. PCT/FR2008/001627, filed Nov. 20, 2008, which claims priority to French Patent Application No. 07/08167, filed Nov. 21, 2007, the disclosure of the prior application is incorporated in its entirety by reference.

TECHNICAL FIELD

The present invention relates to a process for preparing aerogels of individualized carbon nanotubes and applications thereof, especially for the manufacture of composite aerogels and of electrochemical compounds.

The present invention relates, in particular, to aerogels of individualized carbon nanotubes obtained by said process, and also to uses of these aerogels.

Obtaining such carbon nanotube aerogels is of great interest for their industrial applications, in particular in view of the unique properties of carbon nanotubes, and of the very low bulk density and high specific surface area of the aforementioned aerogels.

In the description below, the references between brackets ([ ]) refer to the list of references presented after the examples.

STATE OF THE ART

The materials commonly denoted by "carbon aerogels" are macroscopic materials essentially (and generally exclusively) constituted of carbon, which have an extremely porous structure, resulting in a very reduced bulk density. For more details regarding structures of carbon aerogel type, reference may especially be made to the article "*Les aérogels et le structure alvéolaires: deux exemples de mousses de carbone*" (Aerogels and the cellular structure: two examples of carbon foams) by L. Kocon and T. Piquero, in *L'actualité Chimique*, No. 245-246, pp. 119-123 (March-April 2006) [ref 1].

Carbon aerogels are generally obtained by processes known as "templating". In these processes, schematically, a porous three-dimensional structure of carbon or of a carbon precursor is formed by using a solid structure or a molecular organization of liquid crystal type as a "mold" for the desired structure. This "mold", known as a template, may take various forms depending on the process used. In this context, there are three main families of templating processes that result in carbon aerogels: (1) the use of microporous or mesoporous solids as solid templates ["Nouveaux concepts d'élaboration de matériaux carbonés poreux" (Novel concepts for producing porous carbon-based materials) by C. Vix-Guterl, J. Parmentier, P. Delhaés, in *L'actualité chimique*, No. 245-246, pp. 124-128 (March-April 2006) [ref 2]; and "*Synthesis of highly ordered carbon molecular sieves via template-mediated structural transformation*" by R. Ryoo, S.-H. Soo, S. Jun, in *The Journal of Physical chemistry B*, 103 (37), pp. 7743-7746 (1999) [ref 3]], (2) the templating of carbon in a liquid or gelled medium ["*High thermal conductivity, mesophase pitch-derived carbon foams: effect of precursors on structure and properties*" by J. Klett et al., in *Carbon*, 38, pp. 153-173 (2000) [ref 4] or "*Novel high strength graphitic foams*", by T. Beechem, K. Lafdi, in *Carbon*, 44, pp. 1548-1549 (2002) [ref 5]] and (3) the templating of carbon-based precursors in a liquid or gelled medium ["*Fabrication of nano-structure control of carbon aerogels via microemulsion templated sol-gel polymerization method*", by D. Wu, R. Fu, M. S. Dresselhaus, G. Dresselhaus, in *Carbon*, 44, pp. 675-680 (2005) [ref 6] or "*Preparation and properties of resorcinol formaldehyde organic and carbon gels*", by S. A. Al-Muthtsabeb, J. A. Ritter, in *Adv. Mater.*, 15(2), pp. 101-104 (2003) [ref 7]].

However, none of these methods relate to carbon nanotube aerogels. However the possibility of producing carbon nanotube aerogels is of obvious industrial and scientific interest, in view of the unique mechanical, electrical and chemical properties of carbon nanotubes. Indeed, these are commonly used in composites (Schaffer, M. S. P., Windle, A. H., "Fabrication and Characterization of Carbon Nanotube/poly(vinyl alcohol) Composites", Adv. Mater., 11, pp. 937-941 (1999) [ref 8]), ultracapacitors (Aldissi, M.; Schmitz, B.; Lazaro, E.; Bhamidipati, M.; Dixon, B., "Conducting Polymers In Ultracapacitor Applications", 56.sup.th Annu. Tech. Conf.-Soc. Plast. Eng., (Vol. 2), pp. 1197-1201 (1998) [ref 10]; An, K. H.; Kim, W. S.; Park, Y. S.; Moon, J.-M.; Bae, D. J.; Lim, S. C.; Lee, Y. S.; Lee, Y. H. "Electrochemical Properties of High-Power Supercapacitors Using Single-Walled Carbon Nanotube Electrodes", Adv. Funct. Mater. 11, pp. 387-392 (2001) [ref 11]), catalysis (Yu, R., Chen, L., Liu, Q., Lin, J., Tan, K.-L., Ng, S. C., Chan, H. S. O., Xu, G.-Q., Hor, T. S. A. "Platinum Deposition On Carbon Nanotubes Via Chemical Modification", Chem. Mater. 10, pp. 718-722 (1998) [ref 12]; (Planeix, J. M.; Coustel, N.; Coq, B.; Brotons, V.; Kumbhar, P. S.; Dutartre, R.; Geneste, P.; Bernier, P.; Ajayan, P. M., "Application Of Carbon Nanotubes As Supports in Heterogeneous Catalysis", J. Am. Chem. Soc. 116, pp. 7935-7936 (1994) [ref 13]) and electronic components or systems of nanometric size (Tans, S. J., Verschueren, A. R. M., Dekker, C., "Room-Temperature Transistor Based On A Single Carbon Nanotube", Nature 393, pp. 49-52 (1998) [ref 14]; Bachtold, A.; Hadley, P.; Nakanishi, T.; Dekker, C., "Logic Circuits With Carbon Nanotube Transistors". Science 294 pp. 1317-1320 (2001) [ref 15]). Thus, developing an aerogel material based on carbon nanotubes is of great interest.

Two methods of producing such materials have been reported to date: (1) Yodh et al., "Carbon nanotube aerogels", Advanced Materials, 2007, 19, pp. 661-664 [ref 16]; and (2) Backov et al., French Patent Application No. 06/11143 (Publication No. FR 2 910 458) [ref 17]. However, in both cases, the method uses a dispersion of carbon nanotubes in the presence of surfactants and a sonication step in order to optimize the dispersion. This creates several drawbacks. On the one hand, the carbon nanotubes are shortened by sonication. The diameter/length ratio of the carbon nanotubes in the aerogel is therefore not optimum. This may also result in electrical contact problems between the nanotubes in the final aerogel. On the other hand, the aerogel obtained contains a surfactant compound if the process does not provide a step that aims to remove it. The presence of surfactant may damage the quality of the aerogel, and may hamper its use depending on the envisaged application. Furthermore, surfactants are frequently associated with problems of poor biodegradability. These methods therefore have the drawback that an additional step of removing the surfactant must be provided.

Furthermore, each of the aforementioned two methods uses carbon nanotubes in the form of bundles (i.e. they are not individualized). The specific surface area of the aerogel thus obtained is therefore adversely affected thereby. In any case, the specific surface area of the aerogels currently known is far from being optimal.

There is therefore a real need for a process for preparing carbon nanotube aerogels that overcomes these defects, drawbacks and obstacles of the prior art.

DESCRIPTION OF THE INVENTION

The objective of the present invention is specifically to respond to this need by providing a process for preparing carbon nanotube aerogels characterized in that it comprises the following steps carried out under an inert atmosphere:

(a) reduction of carbon nanotubes by an alkali metal in order to result in a polyelectrolyte salt of carbon nanotubes;

(b) exposure of said polyelectrolyte salt of carbon nanotubes to a polar aprotic solvent in order to result in a solution of individualized reduced carbon nanotubes;

(c) freezing of said solution of individualized nanotubes; and (d) sublimation of the solvent.

Steps a) and b) of the process are always carried out under an inert atmosphere. The expression "inert atmosphere" is hereby understood to refer to a gas or a gas mixture that does not promote the re-oxidation of the carbon nanotubes that have been reduced to neutral nanotubes. For example, the process is carried out under an oxygen-free gaseous atmosphere. In particular, the process may be carried out under an argon or nitrogen atmosphere.

In one embodiment, the alkali metal may be any alkali metal that makes it possible to carry out the present invention. It may be chosen, for example, from the group comprising lithium, sodium, potassium, rubidium and cesium. More particularly, the alkali metal may be lithium, sodium or potassium. In certain particular embodiments, the alkali metal is lithium or sodium. In other particular embodiments, the alkali metal is potassium.

The expression "reduction by an alkali metal" is hereby understood to refer to a reduction in which an alkali metal is involved. Thus, the reduction may take place directly in the presence of an alkali metal, for example in the vapor phase. Reduction methods in the presence of an alkali metal are well known in the art. A person skilled in the art will be able to identify the operating conditions suitable for implementing a reduction process in the presence of an alkali metal, for example in the vapor phase. In particular, a person skilled in the art could be inspired by the methods described in "Synthesis of graphite intercalation compounds", A. Hérold in Chemical Physics of Intercalation, A. P. Legrand and S. Flandrois Eds, NATO ASI Series, series B, Vol. 172, pp. 3-45 (1987) for example [ref 18], which are directly applicable to carbon nanotubes.

In another embodiment, the reduction takes place in the presence of an alkali metal salt obtained from an alkali metal. For example, the reduction may take place in the presence of an alkali metal polyaryl salt of formula $A^+B^-$, in which $A^+$ represents a cation of an alkali metal ion, and $B^-$ represents an anion of a polyaromatic compound. Such alkali metal polyaryl salts and their manufacturing process are described, for example, in C. Stein, J. Poulenard, L. Bonnetain, J. Golé, C. R. Acad. Sci. Paris 260, 4503 (1965) [ref 19]; "Synthesis of graphite intercalation compounds", A. Hérold in Chemical Physics of Intercalation, A. P. Legrand and S. Flandrois Eds, NATO ASI Series, series B, Vol. 172, pp. 3-45 (1987) [ref 20]; F. Béguin and R. Setton, New ternary lamellar compounds of graphite, Carbon 13, 293-295 (1975) [ref 21]; Pénicaud et al., "Spontaneous dissolution of a single-wall carbon nanotube salt", J. Am. Chem. Soc., 127, 8-9, (2005) [ref 34].

According to one embodiment, the polyaromatic compound is chosen from the group comprising naphthalene, phenanthrene, biphenyl, anthracene, perylene, benzophenone, fluorenone, benzoquinone and anthraquinone. In one particular embodiment, the polyaromatic compound is naphthalene. In one particular embodiment, the alkali metal polyaryl salt is a polyaryl salt of potassium (that is to say, a salt of formula $A^+B^-$, in which $A^+$ represents $K^+$). Advantageously, the alkali metal polyaryl salt of formula $A^+B^-$ is a potassium salt of naphthalene ($Naph^-K^+$).

The expression "individualized reduced carbon nanotubes" is understood, in the present application, to refer to a compound comprising at least two individual carbon nanotubes that are negatively charged and neutralized by positive alkali metal counterions in solution in a polar aprotic solvent. Carbon nanotubes generally exist in the form of bundles of nanotubes (i.e., the nanotubes are not individual, they are "agglomerated" into bundles). In the present application, the expression "individualized reduced carbon nanotubes" refers to bundles of carbon nanotubes that are partially deagglomerated, that is to say bundles of carbon nanotubes for which the specific surface area is increased relative to that of the initial bundles (before the implementation of steps a) and b) of the process of the invention). Thus, the expression "individualized reduced carbon nanotubes" may represent a mixture of individual carbon nanotubes and of partially deagglomerated bundles, that are negatively charged and neutralized by positive alkali metal counterions. Preferably, the "individualized reduced carbon nanotubes" predominantly comprise individual carbon nanotubes that are negatively charged and neutralized by positive alkali metal counterions. Preferably, said carbon nanotubes are not in the form of bundles, but are exclusively in the form of individual nanotubes.

The bundles of nanotubes are firstly reduced by an alkali metal in order to form a polyelectrolyte salt of carbon nanotubes (step a) of the process of the invention). The individualization (partial, and preferably complete) of the carbon nanotubes takes place during step b) of the process by exposure to a polar aprotic solvent, which solvates the reduced carbon nanotubes, and thus separates them from one another.

The individualized reduced carbon nanotubes may be in the form of a binary compound of formula $MC_x$ where M represents a positive counterion of an alkali metal ($M^+$) and x represents an integer between 6 and 200. In particular, the alkali metal may be potassium, lithium or sodium.

The individualized reduced carbon nanotubes may be in the form of a ternary compound of formula $M(Solv)_yC_x$ in which M is an alkali metal ion ($M^+$), Solv is a molecule of aprotic solvent, x represents an integer between 6 and 200 and y represents a number between 0 and 8. The molecule of solvent may be a molecule of an aromatic solvent (for example benzene or toluene) or nucleophilic solvent (for example, a solvent for which the structure contains at least one oxygen atom such as THF). For example, the solvent is THF and the polyelectrolyte salt of carbon nanotubes is a ternary compound of structure $Na(THF)_yC_x$, $Li(THF)_yC_x$ or $K(THF)_yC_x$ in which x represents an integer between 6 and 200, and y represents a number between 0 and 8. For example, the ternary compound may correspond to the formula: $K(THF)C_{10}$, $Na(THF)C_{10}$, $Li(THF)C_{10}$ or $Li(THF)C_6$. The number y is not necessarily an integer. Specifically, it may represent an average of the coordination number of the solvent Solv to the alkali metal cation. For example, ternary compounds $M(Solv)_yC_x$ have been prepared and isolated where the variable y was measured as being equal to 0.8. In the present application, for simplicity of writing, the number y is rounded up or down to the nearest higher or lower integer. For example, the ternary compounds of formula $Na(THF)C_{10}$ or $Li(TRF)C_{10}$ referenced above encompass compounds for which the elemental analysis revealed that they were compounds of formula $Na(THF)_{0.8}C_{10}$ or $Li(THF)_{0.8}C_{10}$. Thus, any formula $M(Solv)_yC_x$ referenced in the present application should be understood as representing a compound of formula $M(Solv)_{y\pm0.5}C_x$.

According to one particular embodiment, the reduction step a) is carried out in the presence of a solvent. For example, the solvent may be a nucleophilic solvent. For example, the nucleophilic solvent may be an aprotic solvent, the structure of which contains at least one oxygen atom, in particular THF.

According to one particular embodiment, the reduction step is chosen from the group comprising the reduction by an alkali metal in the vapor phase followed by exposure to an aprotic solvent, electrochemical reduction and reduction by an alkali metal polyaryl salt in an aprotic solvent. For example, the solvent may be an aromatic solvent, such as benzene or toluene. The solvent may be an aprotic solvent, the structure of which contains at least one oxygen atom such as THF.

According to one particular embodiment, the reduction step a) comprises the addition, to the carbon nanotubes, under an inert atmosphere, of an alkali metal polyaryl salt of formula $A^+B^-$, in which:

$A^+$ represents a cation of an alkali metal ion, and $B^-$ represents an anion of a polyaromatic compound.

According to one embodiment, the polyaromatic compound is chosen from the group comprising naphthalene, phenanthrene, biphenyl, anthracene, perylene, benzophenone, fluorenone, benzoquinone and anthraquinone.

According to one particular embodiment, the polar aprotic solvent used in the exposure step b) has a dielectric constant of 25 to 200. For example, the polar aprotic solvent may be sulfolane, dimethyl sulfoxide (DMSO), dimethylformamide, N-methylpyrrolidone or N-methylformamide. In one particular embodiment, the polar aprotic solvent is DMSO. In another particular embodiment, the polar aprotic solvent is N-methylpyrrolidone.

Thus, the process of the invention makes it possible to prepare a carbon nanotube aerogel from an organic polar solution, as opposed to the surfactant-doped aqueous solutions used in the prior art (Yodh et al. and Backov et al.).

This is in no way trivial, and is not obvious from the prior art.

Specifically, polar aprotic solvents such as sulfolane, dimethyl sulfoxide (DMSO), dimethylformamide (DMF), N-methylpyrrolidone (NMP) or N-methylformamide have vapor pressures that are much lower than water. For example, the vapor pressure of DMSO is one order of magnitude lower than that of water at around 0° C. (by way of example, $P_{vap}$ (water)=6 mbar at zero degrees versus $P_{vap}$ (DMSO)=0.2 mbar at 6 degrees).

Furthermore, since freeze drying is frequently used in biology, to the knowledge of the inventors on solutions that are exclusively aqueous or that contain an organic solvent such as DMSO in a minor proportion, commercial freeze dryers are calibrated for water. For this reason, they are not suitable for the freeze drying of organic solutions, particularly polar solvents having a very low vapor pressure such as the aforementioned solvents.

Therefore, a person skilled in the art was not encouraged to explore the freeze drying of solutions of individualized reduced carbon nanotubes in a polar aprotic solvent such as those that are involved in the process of the invention, insofar as it is not aqueous solutions that are being dealt with.

Thus, considering the aforementioned technical difficulties and the physicochemical characteristics of polar aprotic solvents (especially their vapor pressure), the freeze drying of polar aprotic organic solutions before the present invention was not obvious to a person skilled in the art.

The inventors have quite surprisingly discovered that it was possible to freeze dry a polar aprotic organic solution, such as a solution of DMSO, in particular a polar aprotic organic solution containing individualized carbon nanotubes.

One difficulty is to avoid commercial freeze dryers which, as indicated above, are calibrated for aqueous solutions.

For more refractory solvents such as NMP (vapor pressure=$2\times10^{-3}$ mbar at $-30°$ C. ($T_{freezing}=-25°$ C.)), this freeze drying may especially be carried out with a powerful vacuum pump, such as a turbomolecular pump, or even several (at least two) turbomolecular pumps in series.

According to one particular embodiment, the exposure step b) is carried out at a temperature of $-60$ to $285°$ C. For example, the exposure step b) is carried out at a temperature of 0 to 35° C., preferably of 20 to 25° C.

Generally, the process of the invention, in particular the exposure step b), may be carried out with or without stirring. When a stirring system is used, this may be a system of mechanical stirring, magnetic stirring or stirring by bath sonication. Generally, stirring by sonication should be avoided as it can damage the carbon nanotubes. However, bath sonication (as opposed to probe sonication), a gentler method, may aid the solubilization of the carbon nanotubes of step b) in slightly difficult cases. In one particular embodiment, the process is carried out with mechanical stirring. In another embodiment, the process is carried out with magnetic stirring.

According to one particular mode of implementation of the process of the present invention, it is possible to apply, after step (a) and before step (b), a filtration step (a1). For example, when step (a) of the process involves a reduction in the presence of an alkali metal salt obtained from an alkali metal, the filtration may make it possible to separate the liquid phase (for example a solution of $K^+Naph^-$ in THF) from the solid phase comprising the polyelectrolyte salt of carbon nanotubes and optionally non-reduced carbon nanotubes. The polyelectrolyte salt of carbon nanotubes thus obtained may be rinsed one or more times with a suitable solvent. For example, after the filtration step (a1), the polyelectrolyte salt of carbon nanotubes may be rinsed with the same solvent used during step (a), in particular THF. The polyelectrolyte salt of carbon nanotubes thus rinsed may optionally be dried before step (b).

According to one particular embodiment, the process also comprises a centrifugation step (b1), this making it possible to separate any undissolved fraction of the solution of individualized reduced carbon nanotubes after step (b). A person skilled in the art will know how to determine the centrifugation conditions suitable for obtaining a clear solution of individualized reduced carbon nanotubes, that is to say that does not comprise detectable aggregates. For example, the centrifugation may be carried out between 10 and 200 000 g, for 0.1 to 24 hours. In one particular embodiment, the centrifugation step is carried out at 2800 g for 1 hour.

According to one embodiment, the presence of aggregates in the solution during the centrifugation is verified by the naked eye. Thus, a sample of the solution may be withdrawn at various intervals in the centrifugation step in order to determine when this centrifugation will have made it possible to obtain a clear solution (that is to say without aggregates visible to the naked eye). Naked eye examination makes it possible to detect potential aggregates having a minimum size of the order of one tenth of a millimeter (100 microns).

According to one embodiment, the presence of aggregates in the solution during the centrifugation is verified using an optical microscope. Thus, a sample of the solution may be withdrawn at various intervals in the centrifugation step in order to determine when this centrifugation will have made it possible to obtain a clear solution (that is to say without aggregates visible to the optical microscope). Optical microscope examination makes it possible to detect potential aggregates having a minimum size of the order of one micron. In one particular embodiment, the sample of the solution may be analyzed using an optical microscope with a magnification of 20 to 100, or even 400.

The term "nanotube" is understood, within the context of the present description, to refer to a tubular carbon-based structure which has a diameter between 0.5 and 200 nm. These compounds belong to the family known as "nanostructured materials", which have at least one characteristic dimension of the order of a nanometer. For further details regarding these materials and their modes of synthesis, reference may especially be made to the article "Nanotubes from carbon" by P. M. Ajayan (Chem. Rev., vol. 99, p. 1787, 1999) [ref 9].

The process of the invention is very versatile, and has the advantage of being able to be used starting both from single-walled nanotubes and from multi-walled nanotubes, which are less expensive.

Advantageously, use will be made, in step (a) of the process, of single-walled or multi-walled nanotubes having an average diameter between 0.5 and 100 nm.

In one particular embodiment, the carbon nanotubes used in step (a) of the process are single-walled nanotubes having an average diameter between 0.7 and 2.0 nm, preferably between 0.8 and 1.4 nm.

In another particular embodiment, the carbon nanotubes used in step (a) of the process are multi-walled nanotubes having an average diameter between 2 and 20 nm, preferably between 10 and 15 nm.

Furthermore, the average length of the nanotubes used in step (a) is generally between 0.05 and 1000 microns.

Advantageously, the solution of individualized carbon nanotubes prepared in step (b) comprises between 0.1 and 10 g of nanotubes per liter of solution. In one preferred embodiment, the solution of individualized carbon nanotubes prepared in step (b) comprises between 0.1 and 2 g of nanotubes per liter of solution.

According to the invention, the aerogel structure may be obtained by slow or sudden freezing of the solution of individualized reduced carbon nanotubes obtained at the end of step (b) of the process.

According to one particular embodiment, the aerogel structure is obtained by sudden freezing of the solution of individualized reduced carbon nanotubes obtained at the end of step (b) of the process. For this purpose, the freezing step (c) may be carried out by placing said solution obtained in step (b) at a temperature below −50° C., or for example below −80° C., or else, for example, below −100° C., or else, for example, below −150° C., or else, for example, below −180° C., or else, for example, below −190° C. In one particular embodiment, the freezing step is carried out suddenly by immersing the solution of individualized carbon nanotubes in liquid nitrogen.

In one particular embodiment, the solution of individualized carbon nanotubes obtained at the end of step (b) is a solution in DMSO. The freezing of the solution of carbon nanotubes in DMSO may be frozen suddenly by exposure to a temperature well below the freezing temperature of DMSO (especially by immersion in liquid nitrogen). The freezing of the solution of carbon nanotubes in DMSO may also be obtained slowly, that is to say by a gentler method (that does not involve sudden freezing), for example by immersion in a medium thermostatically controlled at a temperature below the freezing temperature of DMSO. For example, the freezing step may be carried out by immersing the solution of carbon nanotubes obtained in step (b) in a bath thermostatically controlled at a temperature below 18° C.

According to one particular embodiment, the structure of the aerogel is obtained by slow freezing of the solution of individualized reduced carbon nanotubes obtained at the end of step (b) of the process. For this purpose, the freezing step (c) is advantageously carried out by immersing the solution of individualized carbon nanotubes obtained in step (b) into a medium thermostatically controlled at a temperature below the freezing temperature of the apolar aprotic solvent used in step (b).

In one particular embodiment, the sublimation step (d) is carried out by low-temperature freeze drying, with or without a thermostatically controlled bath, of the frozen solution of nanotubes. When a thermostatically controlled bath is used, advantageously the sublimation step is carried out by thermostatically controlling the solution of individualized carbon nanotubes at a temperature sufficiently below the freezing temperature of the apolar aprotic solvent used in step (b). In one particular embodiment, the temperature of the thermostatically controlled bath is at least 1° C. below the freezing temperature of the polar aprotic solvent, preferably at least 5° C. below the freezing temperature of the polar aprotic solvent.

In one particular embodiment, the sublimation step (d) is carried out at a pressure less than or equal to $10^{-2}$ mbar, preferably less than or equal to $10^{-3}$ mbar, preferably less than or equal to $10^{-4}$ mbar, more advantageously less than or equal to $10^{-5}$ mbar. In one particular embodiment, the sublimation step (d) is carried out at a pressure of $10^{-6}$ mbar. A powerful vacuum pump may be used in order to obtain the pressure suitable for carrying out the sublimation. A freeze dryer, designed for aqueous solutions, is not sufficient to obtain the aerogel. For example, a judicious control of parameters such as the refrigeration temperature (choice of the cooling bath to keep the organic solution frozen), and the vacuum applied (choice of a suitable vacuum pump to obtain a satisfactory vacuum, need to eliminate the rubber connections often used in freeze dryers (i.e. use of a "direct" connection between the chamber containing the solution to be freeze dried and the vacuum pump), and to ensure that the volume of the vacuum chamber is not too large relative to the volume of solution to be evaporated) is necessary. In one embodiment, the freeze drying is carried out with a vacuum pump capable of generating a pressure of less than 0.1 mbar. Depending on the nature of the solvent, in particular its vapor pressure, a turbomolecular pump may be used.

Depending on the requirements, the aerogel may be shaped before or after the sublimation (or freeze drying). For example, the aerogel may be "molded" by choosing the appropriate shape of the container in which the frozen solution is sublimed (or freeze dried). The aerogel may also be formed into thin membranes after sublimation (or freeze drying) by compression of the aerogel.

In one particular embodiment, the sublimation step (d) is carried out with a sufficiently powerful pump in order to obtain, above the frozen solution, a pressure below the saturation vapor pressure of the solvent. Furthermore, in order to optimize the vacuum, the sublimation device may be designed so that there is a direct connection between the tube to be freeze dried and the pump. Such a device makes it possible to avoid using rubber tubing which has the drawback of "degassing" and not making it possible to obtain the vacuum required for the sublimation, in particular for polar organic solvents such as DMSO. Furthermore, this direct connection allows a passage from the chamber under an inert atmosphere used for the preparation of the solution of carbon nanotubes to the vacuum pump, without exposing the solution to the air (which would result in the oxidation of the nanotubes, and therefore in their reaggregation).

In one particular embodiment, the polar aprotic solvent used in step (b) is DMSO and the sublimation step is carried out by thermostatically controlling the solution of carbon nanotubes in DMSO at a temperature below 18° C. (freezing temperature of DMSO), for example 6° C. In this particular embodiment, the sublimation step (d) is carried out at a pressure less than or equal to $10^{-2}$ mbar, preferably less than or equal to $10^{-3}$ mbar, preferably less than or equal to $10^{-4}$ mbar, more advantageously less than or equal to $10^{-5}$ mbar. In one particular embodiment, the polar aprotic solvent is DMSO and the sublimation step (d) is carried out at a pressure of $10^{-5}$ mbar.

According to another aspect, the present invention also provides carbon nanotube aerogels obtainable by a process according to the invention. For example, the aerogels may be used as they are, or may be deposited on a substrate or mixed with another material.

At the end of the process of the invention, a material based on individualized carbon nanotubes, which is generally monolithic, is obtained. The material obtained has the shape of the frozen solution, but only a percolated (contact) network of individualized carbon nanotubes remains.

The aerogels of the invention furthermore have a very low bulk density, in particular much lower than those of the currently known carbon nanotube aerogels. For example, Yodh et al. [ref 16] report aerogels having a density between 10 and 30 mg/cm$^3$. Backov et al. [ref 17] report bulk densities "typically in the vicinity of 0.2 g/cc" (that is to say 200 mg/cm$^3$). Thus, generally, an aerogel as obtained according to the invention has a bulk density usually less than or equal to 10 mg/cm$^3$, generally less than or equal to 5 mg/cm$^3$, preferably 2±0.5 mg/cm$^3$. An aerogel as obtained according to the invention has a bulk density between 0.1 and 10 mg/cm$^3$, generally between 0.1 and 5 mg/cm$^3$, preferably between 0.1 and 2±0.5 mg/cm$^3$.

This very low bulk density results in a very high pore volume for the aerogels of the invention where, usually, the volume occupied by the pores represents at least 99% of the total volume of the aerogel, generally at least 99.5%, or even at least 99.8%. As will readily be apparent to a person skilled in the art, the pore volume may be influenced by the concentration of the solution of individualized carbon nanotubes obtained in step (b). The pore volume of the aerogel could therefore be increased by using a solution of individualized carbon nanotubes of lower concentration. It will be appreciated, however, that the mechanical strength of the final aerogel will probably be lower. It will therefore be advisable to adapt the concentration of the solution of individualized carbon nanotubes as a function of the application for which the aerogel is intended.

Generally, the concentration of the solution of individualized carbon nanotubes is between 0.01 and 10 mg/g or between 0.001 and 1% v/v, advantageously between 0.1 and 4 mg/g or between 0.01 and 0.4% v/v, more advantageously between 1 and 2 mg/g or between 0.1 and 0.2% v/v. Generally, the concentration of the solution of individualized carbon nanotubes is of the order of 1 mg/g or 0.1% v/v.

Generally, the carbon aerogels thus obtained have a structure of high porosity. These are open and closed porosities, the latter possibly being considered to be negligible. A material with open porosity is understood to refer to a material in which all of the pores communicate with the surface of the material. Closed porosity corresponds to the internal volume of the carbon nanotubes.

The aerogels obtained according to the process of the invention also have a specific surface area greater than that of the carbon nanotube aerogels known to date (due to the fact that, in the present aerogels, the carbon nanotubes are individualized). Therefore, the aerogels of the invention usually have a high specific surface area, in general between 100 and 2000 m$^2$/g, this specific surface area advantageously being greater than 200 m$^2$/g, preferably greater than 250 m$^2$/g, preferably greater than 300 m$^2$/g. Within the meaning of the present description, the expression "specific surface area" refers to the BET specific surface area, as determined by nitrogen adsorption, according to the well-known method known as the Brunauer-Emmet-Teller method which is described in *The Journal of the American Chemical Society*, volume 60, page 309 (1938) and that corresponds to the international standard ISO 5794/1.

A specific surface area as high as 2000 m$^2$/g may be observed in particular if a certain proportion of the tubes are open.

Furthermore, the monolithic nature (all in one piece) of the aerogel, apart from providing an electrical contact, permits a certain mechanical strength.

This particular structure of the aerogels of the invention may especially be highlighted on images of the materials obtained by field-effect scanning electron microscopy, examples of which are given in the appended figures. Observed therein are, in particular, two types of open porosity: volume pores having a diameter of the order of 20 microns and two-dimensional pores (holes in the walls of the first pores) having a diameter of 10 to 100 nanometers.

The aerogels obtained according to the present invention are electrically conductive. For this reason, they may advantageously be used for the preparation of electrochemical components. For example, they could replace the carbon electrodes in fuel cells, biosensors and/or ultracapacitors, due to their high specific surface area. The increased porosity compared to conventional carbon electrodes should give quantitative leaps in terms of performance for energy applications (fuel cells, biosensors, ultracapacitors).

The particular structure of the carbon aerogels obtained according to the invention makes them particularly suitable as separation materials, especially for carrying out separations of liquid/liquid type. In particular, the aerogels of the present invention are suitable for the adsorption of hydrophobic molecules, especially that are present in aqueous media. Thus, one application of the aerogels of the present invention relates to the decontamination of aqueous media containing hydrophobic pollutants such as hydrocarbons for example.

In this context, the high porosity of the aerogel makes it possible to obtain a good diffusion of the species, thus leading to high separation rates. In this context, the aerogels of the invention may, for example, be used for preparing filtration materials or membranes, especially for the filtration or else for the cleanup of wastewaters.

To this end, the teaching of French patent application No. FR 2 881 362 [ref 22] may be adapted in order to implement pollution control devices that use the aerogels of the invention. The well-known difference between the present aerogels and the carbon-based nanostructured materials of the aforementioned patent application is their unmatched bulk density. For this purpose, the aerogels of the present application therefore represent a more advantageous and more effective alternative to the materials described in application FR 2 881 362 in order to retain the hydrophobic species of aqueous media.

The aerogels may be used in the form of membranes by compression of said aerogel. They may therefore be used as filtration and/or pollution-control membranes, especially for cleaning up oil slicks. The high specific surface area of the aerogels according to the invention, and also their hydrophobicity, allows the preferential adsorption of oil in an oil/water mixture. Thus, said aerogels make it possible to envisage solutions to pollution problems, in particular for water treatment or the treatment of oil spills, by adsorption of the hydrocarbons present in an aqueous medium, while there is not currently a high-performance means to solve these pollution problems.

Considering their specific structure, the aerogels of the invention are also well suited to other applications. In particular, due to the biocompatible nature of the carbon, they may especially be used for preparing biomaterials, and in particular for preparing a support for cell growth, for bone growth or for cartilage replacement. They may especially find an application for the preparation of biocompatible supports for the growth of bone cells, or of neurons. In this type of application, the particular porosity of the material ensures an optimum colonization: the porosity ensures, on the one hand, a diffusion of the cells which may reach substantially the whole of the surface of the material and, on the other hand, an irregularity of the surface of the material suitable for ensuring a good fixation of the cells to the aerogel.

In certain embodiments, in order to ensure an optimum topology for cell growth, the solution of individualized reduced carbon nanotubes obtained in step (b) may be filled with beads that are insoluble in the polar aprotic solvent in question. After freeze drying, the aerogel forms around these beads. Thus, the process of the invention may also comprise a step (b1) of addition of beads of material that is insoluble in the polar aprotic solvent of step (b). Said beads may have a diameter between 10 microns and 1 mm, preferably between 50 and 100 microns.

The beads may then be removed by dissolving or acid attack, leaving an aerogel with controlled pores. The use of such spherical particles as "templates" is very widespread in the scientific literature and a person skilled in the art can easily apply and/or adapt this technique to the solutions of reduced carbon nanotubes described here.

The aerogels may be used in the form of membranes by compression of said aerogel. The elastic nature of these membranes (due to the presence of pores), and also their excellent wear resistance and their biocompatibility, make these materials particularly advantageous candidates for applications in the field of cartilage replacement.

It should be noted that since the aerogels of the prior art are prepared from aqueous suspensions of carbon nanotubes in the presence of non-biocompatible surfactants (cf. works by Yodh et al. and Backov et al.), they are not really suitable for biomedical applications. Even though Yodh et al. describe a step of removing the surfactant used, uncertainty remains as to the possible presence of surfactant residues. Furthermore, this requires an additional step of removing surfactants which is not necessarily easy to carry out, or even advantageous from an industrial standpoint. The aerogels of the present invention therefore have a considerable technical advantage for the production of novel biocompatible materials.

More generally, the aerogels of the invention may be used in most of the known applications of carbon-based aerogels, insofar as they have the specific advantages of these materials, in particular a high chemical inertia, especially with respect to reducing agents, a high thermal stability up to more than 2000° C. (in a non-oxidizing medium), and also very good thermal and electrical conductivity.

The aerogels of the invention may thus, in particular, be used for preparing a support for catalytic species, for example for the catalysis of reactions in a reducing medium, especially at high temperature. Thus, for certain applications, the aerogels obtained may be post-treated, for example in order to be impregnated by catalytic species. In one particular embodiment, the aerogels are used for the preparation of catalyst supports for heterogeneous catalysis.

Impregnated, for example, with silicon, resins or polymers, the aerogels may also make it possible to obtain conductive composites, due to their percolated (contact) network. Thus, the present invention also relates to the use of the aerogels obtainable by the process of the invention for the preparation of composites.

The term "impregnated" is understood here to refer to an impregnation of the aerogel with a material, either:
(i) by soaking the aerogel with another material, in liquid form or in solution, that penetrates into the porosity of the aerogel. Thus, according to this particular embodiment, the process of the invention also comprises a step (e) that consists in soaking said aerogel with another material, in liquid form or in solution. This may be, for example, a polymer, a blend of polymers or a resin, in liquid form or in solution, or molten silicon. The aerogel is thus soaked with said material in liquid form or in solution; or
(ii) by mixing a solution of a material with the solution of individualized carbon nanotubes obtained at the end of step (b) of the process of the invention. The material may be, for example, a polymer, a mixture of polymers, or a resin. Thus, according to this particular embodiment, the process of the invention also comprises, before the freezing step (c), a step (b2) of mixing a solution of a material (for example a solution of polymer, of a blend of polymers, or of a resin) with the solution of individualized reduced carbon nanotubes obtained in step (b). The mixture is then frozen and sublimed according to steps (c) and (d) of the process in order to form a composite aerogel.

The resins used may be unsaturated polyester resins (used, for example, in glass-fiber-reinforced plastics), epoxy resins (used, for example, in adhesives and in the manufacture of plastics), phenolic resins or polyimide resins.

According to the invention, the polymer may be any polymer that makes it possible to implement the present invention. It may be chosen, for example, from the group comprising polystyrene; polyolefins, for example polyethylene, polypropylene, poly($\alpha$-olefin)s, poly-isobutene and polypropylene; polyethers; polyesters; polyamides; polyacrylamides; polyacrylates (for example, polymethyl methacrylate or "PMMA"); polysilanes; polysiloxanes.

According to the invention, the polymer may be a linear block copolymer or a random copolymer. A person skilled in the art will know how to identify suitable operating conditions and the polymer(s) to be used in order to produce a composite having the required/desired properties. In particular, a person skilled in the art will be able to take inspiration from the methods described in FR 04/05120 [ref 29] and/or WO 2006/136715 [ref 30] which describe the preparation of composites from carbon nanotubes and polymers or blends of polymers. A person skilled in the art will know how to adapt the methods described in these documents in order to carry out the preparation of composite aerogels from aerogels obtainable by the process of the present application. The polymer(s) may be selected so as to optimize the polymer/carbon nanotubes surface interactions.

The expression "block copolymer" is understood in the present application to refer to a sequential polymer comprising more than one monomer species. In a block copolymer, identical monomers are grouped. Such polymers and their manufacturing process are described, for example, in Matyjaszewski, K.; Eds.; Advances in Controlled/Living Radical Polymerization, (American Chemical Society 2003) [ref 23] or Hsieh, H. L.; Quirk, R. P.; Eds.; Anionic Polymerization Principles and Practical Applications, (Marcel Dekker 1996) [ref 24].

The expression "random copolymer" is understood in the present application to refer to a polymer in which the various monomers are mixed up as a function of the reactivity and of the concentration of the latter. Such polymers and their manufacturing processes are described, for example, in Matyjaszewski, K.; Davies, T. P.; Eds.; Handbook of Radical Polymerization, (Wiley-Interscience 2002) [ref 25] or Fontaine, L.; Initiation à la Chimie et à la Physico-Chimie Macromoléculaires [Introduction to macromolecular chemistry and physical chemistry] (Groupe Français d'Etudes et d'Applications des Polymères [French Group of Polymer Studies and Applications] (Chapter 3)) [ref 26].

According to the invention, when it is a question of a block copolymer, it may be, for example, a diblock copolymer synthesized, for example, by controlled radical polymerization or by living anionic polymerization or by living cationic polymerization or a random copolymer synthesized by controlled radical polymerization or uncontrolled radical polymerization.

Controlled radical polymerization (CRP) is a method of choice for preparing well-defined polymers and copolymers with adjustable molecular weights and low polydispersity indices. Techniques that can be used in the present invention are described, for example, in Matyjaszewski, K.; Davies, T. P.; Eds.; Handbook of Radical Polymerization, (Wiley-Interscience 2002) [ref 25].

The expression "living polymerization" is understood to refer to a polymerization in which there are neither termination reactions nor transfer reactions, and where the polymer chains continue to grow as long as there remain monomer molecules to add to the chains. According to the invention, the living polymerization may be cationic or anionic. Such processes are described, for example, in Matyjaszewski, K.; Eds.; Cationic Polymerizations Mechanisms, Synthesis, and Applications, (Marcel Dekker 1996) [ref 31] or Hsieh, H. L.; Quirk, R. P.; Eds.; Anionic Polymerization Principles and Practical Applications, (Marcel Dekker 1996) [ref 24].

The monomers may be introduced in their entirety during the polymerization step. They may also be introduced separately or as a mixture, continuously or in batch mode. Additional monomer may also be introduced at the end of the polymerization in order to obtain the desired polymer composition.

The adjuvants optionally incorporated during conventional polymerization processes can be used according to the process of the invention. Thus, it is possible to use initiators, chain transfer agents, catalysts, antioxidants and lubricants known to a person skilled in the art.

(i) Impregnation by Soaking the Aerogel with Another Material

According to one embodiment, the composite is obtained by impregnating an aerogel obtained according to the invention with another material, in liquid form or in solution, for example silicon, a polymer or blend of polymers, or a resin.

The term "impregnation" is understood here to refer to an impregnation of the aerogel by soaking the latter according to the embodiment (i) above.

Thus, in one particular embodiment, the process also comprises an additional step (e) which consists in soaking the aerogel of the invention with another material (for example a polymer, a blend of polymers or a resin, in liquid form or as a solution thereof, or molten silicon), said material being in liquid form or in solution. For example, the aerogel may be soaked with PMMA or with a solution of PMMA. For example, the PMMA may be in solution in the same solvent as the reduced nanotubes of step (b). For example, this solvent may be sulfolane, dimethyl sulfoxide (DMSO), dimethylformamide, N-methylpyrrolidone or N-methylformamide. In one particular embodiment, the solvent is DMSO. In another particular embodiment, the solvent is N-methylpyrrolidone.

Said step (e) may be followed by a step of solidification of the composite aerogel, by drying, in order to remove the solvent, for example by heating the impregnated aerogel, optionally under reduced pressure, so as to evaporate the solvent from the pores of the aerogel.

As regards the impregnation of the aerogels of the invention with silicon, this may enable, on the one hand, the densification of the aerogel and, on the other hand, the combination of the properties of silicon carbide (hardness and high-temperature stability) with the porosity of the aerogel.

Thus, in one particular embodiment, the aerogel of the invention may be impregnated with molten silicon. Since the aerogel is composed of carbon nanotubes, this impregnation with silicon is in this case a reactive impregnation: the silicon then reacts with the carbon to form silicon carbide.

The expression "impregnation with silicon" is understood here to refer to an impregnation of the aerogel with a molten silicon type phase that penetrates into the porosity of the aerogel.

Molten silicon is very fluid and has a high wetting power especially with respect to surfaces made of carbon. Thus, when an aerogel according to the invention is impregnated with silicon in the liquid state, this silicon advances into the network of porosities of the material following the surface of the pores.

In another particular embodiment, the aerogel may be impregnated with a composition containing an organo-silicon compound in solution, for example an organo-silicon compound that is a precursor of silicon carbide such as polycarbosilane.

In another particular embodiment, the aerogel of the invention may be impregnated with silicon and/or germanium (that is to say with silicon alone, with germanium alone or a mixture of silicon and germanium in any proportion).

In another particular embodiment, the aerogel of the invention may be predominantly impregnated with silicon and/or germanium alloyed with at least one metal or another metalloid. In the latter case, the metal or other metalloid may be chosen, in particular, from iron, cobalt, titanium, zirconium, molybdenum, vanadium, carbon or boron depending on the particular properties to be conferred to the aerogel after impregnation with silicon.

A person skilled in the art will know how to identify suitable operating conditions in order to implement a process for impregnation of the aerogel of the invention with silicon and/or germanium, optionally alloyed with at least one metal or another metalloid. For example, reference could be made to the international patent application published under the No. WO 2004/076381 [ref 36].

(ii) Impregnation with a Mixture of a Solution of a Material with the Solution of Individualized Carbon Nanotubes Obtained at the End of Step (b)

According to another embodiment, the composite is obtained by a process comprising a step (b2) of mixing a solution of a material with the solution of individualized carbon nanotubes obtained in step (b). Said material may be, for example, a polymer, a blend of polymers, or a resin. The material may be in solution in the same solvent as that used to form the solution of individualized carbon nanotubes obtained in step (b). For example, it may be sulfolane, dimethyl sulfoxide, dimethylformamide, N-methylpyrrolidone or N-methylformamide. In one particular embodiment, the solvent is DMSO. In another particular embodiment, the solvent is N-methylpyrrolidone.

Thus, according to this particular embodiment, the process of the invention also comprises, before the freezing step (c), a step (b2) of mixing a solution of a material with the solution of individualized carbon nanotubes obtained in step (b). The mixture is then frozen and sublimed according to steps (c) and (d) of the process in order to form a composite aerogel. It is understood that the various embodiments of steps (c) and (d) described in the present document can also be applied to the implementation of a composite aerogel according to the embodiment (ii) described above.

Several variants of the embodiment (ii) may be implemented.

Thus, according to one embodiment, the process according to embodiment (ii) comprises a step of in situ polymerization of a monomer or blend of monomers in said solution of individualized reduced carbon nanotubes. Such polymers and their manufacturing process are described, for example, in Matyjaszewski, K.; Eds.; Advances in Controlled/Living Radical Polymerization, (American Chemical Society 2003) [ref 23]; Hsieh, H. L.; Quirk, R. P.; Eds.; Anionic Polymerization Principles and Practical Applications, (Marcel Dekker 1996) [ref 24]; Matyjaszewski, K.; Davies, T. P.; Eds.; Handbook of Radical Polymerization, (Wiley-Interscience 2002) [ref 25] or Fontaine, L.; Initiation à la Chimie et à la Physico-Chimie Macromoléculaires [Introduction to macromolecular chemistry and physical chemistry] (Groupe Français d'Etudes et d'Applications des Polymères [French Group of Polymer Studies and Applications] volume 12 (Chapter 3)) [ref 26].

According to one embodiment, the process according to the embodiment (ii) comprises a step of polymerization/grafting of one or more monomers to one or more individualized carbon nanotubes. Polymerization/grafting methods are well known in the art. A person skilled in the art will know how to identify suitable operating conditions for implementing a process of polymerization/grafting of a monomer to one or more individualized carbon nanotubes.

According to one particular embodiment, the individualized carbon nanotubes are functionalized with one or more grafts of functional groups before their association with the polymer(s). In this context, the term "association" is understood to refer to the combination of the grafted carbon nanotubes with the polymer(s) by simple mixing, by in situ polymerization of a monomer or blend of monomers in a solution of grafted carbon nanotubes, or by polymerization/grafting of one or more monomers to one or more grafted carbon nanotubes. The attachment of said functional groups to the carbon nanotubes may be carried out by any suitable organic chemistry process known to a person skilled in the art. For example, a general overview of methods of functionalizing carbon nanotubes can be found in: "Chemistry of Carbon Nanotubes" by Dimitrios Tasis, Nikos Tagmatarchis, Alberto Bianco and Maurizio Prato, Chem. Rev. 2006, 106, 1105-1136 [ref 33]. These may be, for example, grafts of polyethylene glycol groups or of acid groups. These grafts may (i) enable a functionalization of the individualized carbon nanotubes, (ii) increase the interactions between the individualized carbon nanotubes (van der Waals type bonds, hydrophobic bonds or hydrogen bonds), and/or (iii) increase the interactions between the individualized carbon nanotubes and the polymer(s) with which they are associated, and may have the advantage of reinforcing the composite aerogels comprising these individualized carbon nanotubes.

According to one particular embodiment, the composite is obtained from a solution of individualized carbon nanotubes and a solution of PMMA, for example in DMSO. Thus, according to this particular embodiment, a PMMA/carbon nanotubes composite aerogel may be obtained by introducing, before the freezing step (c), a step of mixing a solution of PMMA (for example in DMSO) with the solution of individualized reduced carbon nanotubes obtained in step (b). The mixture is then frozen and sublimed in order to form a PMMA/carbon nanotubes composite aerogel.

The composite aerogels according to the invention may be used in all of the applications provided for the aerogels of the invention while giving them a better mechanical strength. For example, these composite aerogels may be used as separation materials (e.g. filtration membranes, pollution-control membranes to be spread over an aqueous surface in order to absorb hydrocarbons), as heterogenous catalysis supports, or as biomaterials (in the case of biocompatible polymers).

According to one particular embodiment of the use of the process of the invention for the preparation of composite aerogels, the composite aerogel may comprise, in addition to the carbon nanotubes, other materials conventionally used in composites.

The fillers that are incorporated into the composition of said composite aerogels may be of nanometric and/or micrometric dimension.

In the present application, the expression "material of nanometric dimension" is understood to refer to a material whose size is a few nanometers in at least one of the spatial dimensions. For example, the size of the material in at least one of the spatial dimensions is between 1 and 20 nm, preferably between 1 and 2 nm.

In the present application, the expression "material of micrometric dimension" is understood to refer to a material having a size between 1 and 100 microns.

The composite may comprise fillers of micrometric dimension only, or nanometric dimension only, or a mixture of micrometric and nanometric fillers (see, for example, FR 2 873 381 [ref 32] where composites comprising nanometric fillers and micrometric fillers in the same material are described).

These various uses of the aerogels of the invention also constitute one particular subject of the invention.

Unexpectedly, the carbon nanotube aerogels of the invention and their specific advantages are obtained very simply by the succession of steps (a) to (d) of the process of the invention.

The process of the invention has, inter alia, the advantage of being simple to use and inexpensive.

Various features and diverse advantageous embodiments of the process of the invention will now be described in greater detail.

The process described in the present invention solves the current major problems with the development of carbon nanotube aerogels. On the one hand, the process of the present invention involves the freeze drying of a solution of carbon nanotubes in a polar aprotic solvent. An advantage of this process, compared to the processes of the prior art which are based on the freeze drying of aqueous dispersions, is that the use of an organic solvent allows a better homogeneity of the solution to be freeze dried and a greater flexibility as regards the incorporation of complementary constituents, for example a polymer or blend of polymers with a view to preparing a composite.

On the other hand, the process of the present invention does not require the use of surfactants. Neither does it require the use of sonication, which damages the carbon nanotubes or at the very least shortens them. Thus, the length/diameter ratio of the carbon nanotubes in the aerogel obtained is maximal.

Indeed, as attested to by numerous publications, it is widely known that ultrasound treatment (sonication) affects the structural integrity of carbon nanotubes. In particular, sonication may give rise to the breakage of carbon nanotubes, and the appearance of defects such as buckling or bending and/or dislocations in the carbon-based structures.

Sonication also causes the tearing of the upper layers of graphite sheets, in the case of multi-walled tubes, which results in a thinning of the nanotubes in a similar manner to the damage brought about by oxidation. Reference may be made, for example, to Lago et al., "Mechanical damage of carbon nanotubes by ultrasound", *Carbon*, 34(6) 814-816, (1996) [ref 37]; Badaire et al., "In situ measurement of nanotube dimensions in suspensions by depolarized dynamic light scattering", *Langmuir*, 20: 10367-10370 (2004) [ref 38]; Heller et al., "Concomitant length and diameter separation of single-walled carbon nanotubes", *J. Am. Chem. Soc.*, 126: 14567-14573 (2004) [ref 39]; Hennrich et al., "The mechanism of cavitation-induced scission of single-walled carbon nanotubes", *J. Phys. Chem. B*, 111: 1932-1937 (2007) [ref 40].

Sonication may also lead to an impairment of the performances, especially electrical performances, of the carbon nanotubes, due to the aforementioned structural damage. See, for example, Badaire et al. [ref 38].

The studies by Yodh et al. [ref 16] and by Backov et al. [ref 17] relate to obtaining aerogels by freeze drying or critical-point drying of an aqueous suspension of carbon nanotubes containing surfactants, which suspension has previously been subjected to an ultrasound treatment, a mechanical process that impairs the structure of the carbon nanotubes, and their electrical properties.

In contrast, in the process of the invention, the carbon nanotubes are individualized by a chemical method known as "mild dissolution" that consists in reducing the carbon nanotubes with an alkali metal and dissolving the polyelectrolyte salt obtained in a polar aprotic solvent. Thus, the process of the invention respects the structure of the carbon nanotubes which is found unaltered in the aerogel. See, for example, FIG. 3 which illustrates Raman spectra of raw carbon nanotubes and of an aerogel of the present invention. As shown in FIG. 3, the two curves (raw nanotubes and aerogel) cannot be differentiated. In particular, the "D" band at 1300 $cm^{-1}$, the signature of disorder and the "RBM" band at around 200 $cm^{-1}$ that are sensitive to the environment of the tube, cannot be differentiated. This observation has been verified at two different wavelengths of the Raman laser.

Furthermore, sonication gives rise to the fragmentation of the carbon nanotubes, which implies the presence of carbon particles and debris in the final product. This drawback is not found in the aerogels of the invention.

Thus, the aerogels of the present invention are superior to the aerogels of the prior art in that they do not have the aforementioned drawbacks due to the sonication process.

Furthermore, one advantage of the process of the invention compared to the processes of the prior art which are based on the freeze drying of dispersions in the presence of surfactants, is that the dissolution of the nanotubes in an organic polar aprotic solvent allows a better homogeneity of the solution to be freeze dried. Indeed, as is shown in FIG. 4, after dissolution according to the process of the invention, the tubes are all exfoliated unlike the raw tubes dispersed in ethanol, which remain as large bundles. Thus, in an aerogel obtained by dispersion and surfactants, there is a large size distribution of the nanotubes when sonicated little and very small lengths when sonicated a lot. See the article by Islam et al., "High weight fraction surfactant solubilization of single-wall carbon nanotubes in water", Nanoletters, Vol. 3(2): 269-273 (2003) [ref 41].

Thus, the process of the invention makes it possible to obtain an aerogel from individualized carbon nanotubes, that is to say by complete exfoliation of the bundles of nanotubes.

Moreover, the aerogels according to the invention are biocompatible. Thus, besides the conventional applications of carbon nanotubes (composites, electronic components, etc.), the present aerogels may be used as biomaterials in biomedical applications, for example as a support for the growth of cells, especially bone cells.

In addition, the process of the invention makes it possible to prepare biocompatible carbon nanotube aerogels, which is extremely advantageous for all biological applications.

Finally, the process works just as well with single-walled carbon nanotubes as with multi-walled nanotubes.

As will be apparent to the person skilled in the art upon reading the present description, one of the main advantages of the present invention is the possibility of obtaining a biocompatible material that is particularly suitable for cell growth. Other advantages include the simplicity of implementation of the process, and also its ability to provide carbon nanotube aerogels of very low bulk density.

Other advantages will also appear to a person skilled in the art on reading the examples below, illustrated by the appended figures, given by way of illustration.

EXAMPLES

Unless otherwise indicated, all the experiments were carried out under an inert atmosphere, for example under argon or nitrogen. In particular, the manipulations were carried out in a glovebox under a dry argon atmosphere ($O_2$ content<10 ppm, $H_2O$ content<10 ppm).

Example 1

Preparation of an Aerogel of Carbon Nanotubes from a Solution of a Polyelectrolyte Salt of Carbon Nanotubes in DMSO The preparation of a solution of a polyelectrolyte salt of carbon nanotubes may be carried out according to the method described in WO 2005/073127 [ref 35]. A variant of this method is described below:

Preparation of a Potassium Salt of Naphthalene (Naph⁻ K⁺)

100 mg of naphthalene were placed in a 250 cm³ round-bottomed flask, added to which were 30 mg of potassium in small pieces having a shiny surface (peeled off with a scalpel just before use), then around 100 cm³ of THF. The round-bottomed flask was heated at reflux until the solution took on a very dark green color and was left at reflux for several hours.

Reduction of Carbon Nanotubes

The solution obtained above was then poured, while filtering in order to avoid an excess of solid potassium, over 55 mg of raw nanotubes (synthesized using the electric arc technique). The whole mixture was left, under magnetic stirring, at ambient temperature for about 15 hours. Alternatively, the reduction in the Naph⁻ K⁺ concentration could be monitored by UV/visible spectroscopy. The reaction mixture was filtered over a membrane of Millipore® type (porosity of 0.45 microns). The solid was rinsed several times with THF (distilled over a potassium/naphthalene mixture), until the THF remained colorless after passing through the filter. The solid was then dried under vacuum at ambient temperature. The solid had a good stability during storage of at least several months, under a controlled atmosphere.

Preparation of a Solution of Individualized Reduced Carbon Nanotubes in DMSO 40 mg of the salt of nanotubes obtained above were subjected to magnetic stirring for around 15 hours in 16 cm³ of DMSO at ambient temperature. The solution obtained was centrifuged at 4000 rpm for 1 hour, then decanted. A homogeneous solution of individualized carbon nanotubes, that is to say that did not comprise aggregates visible using an optical microscope (magnification=400). Said solution contained 2 mg of reduced carbon nanotubes per gram of DMSO.

Figure 1A:
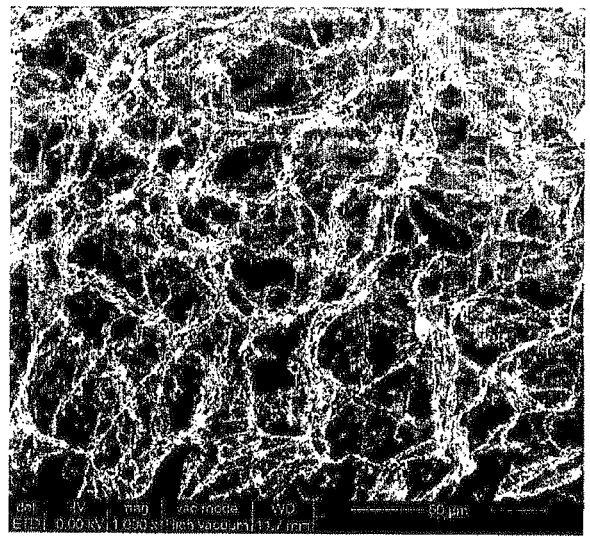
FIG. 1 represents scanning electron microscopy (field-effect microscope) images of an aerogel sample obtained according to the process of the invention at ×1000 (FIG. 1A), ×3000 (FIG. 1B) and ×60 000 (FIG. 10) magnifications.
Figure 1B:
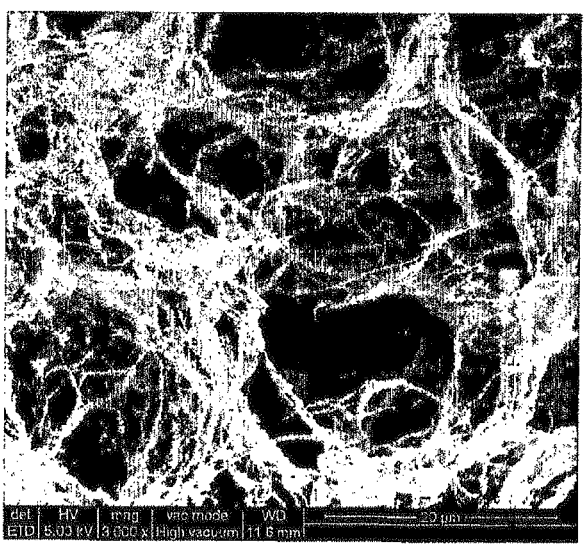
Figure 1C:
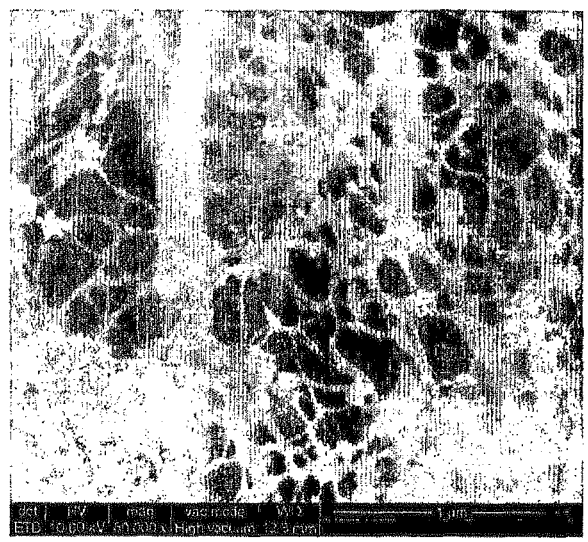
Figure 2:
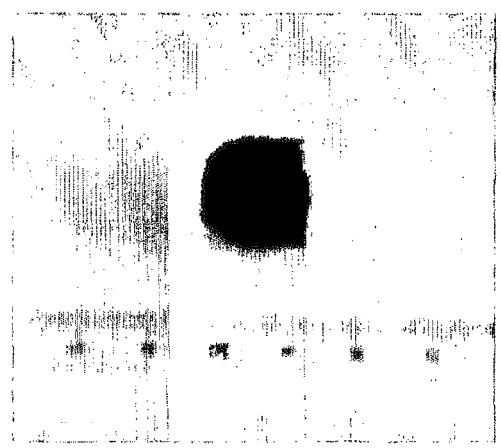
FIG. 2 represents a photograph of an aerogel obtained according to the process of the invention.
Figure 3:
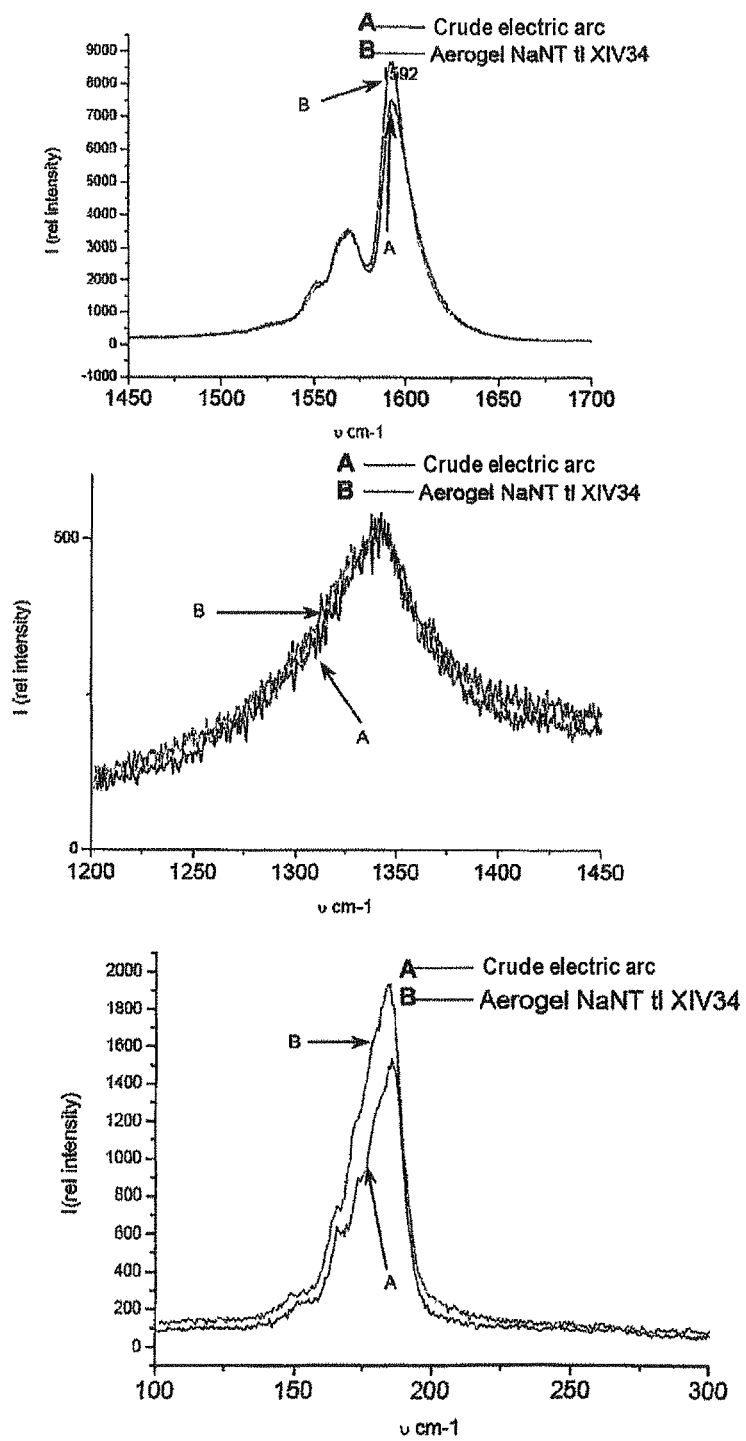
FIG. 3 represents Raman spectra of raw carbon nanotubes and of an aerogel of the present invention.
Figure 4:
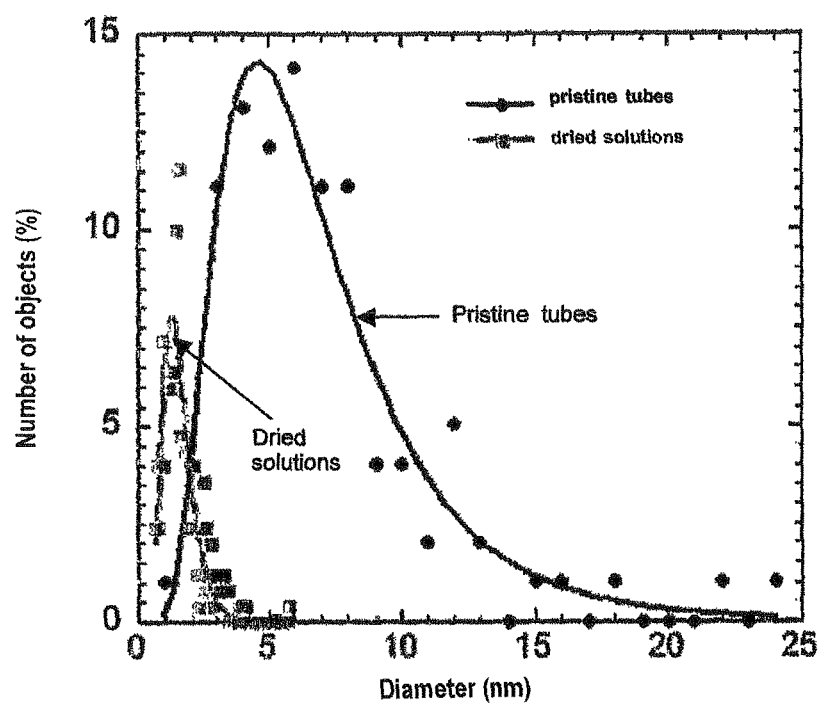
FIG. 4 represents the distribution of the diameter of the carbon nanotubes that is observed after drying of the solution of individualized reduced carbon nanotubes obtained at the end of step (b) of the process of the invention (narrow left-hand curve) compared to raw carbon nanotubes in bundles (broad right-hand curve).

Freeze Drying of the Solution of Individualized Reduced Carbon Nanotubes in DMSO From 1 to 6 g of the preceding solution were placed in a glass test tube equipped with a valve which (i) made it possible to hermetically seal the contents of the test tube and (ii) had a means of connection to the vacuum pump (of Swagelok type for example). The tube was filled with solution under an inert atmosphere, the valve was sealed and the tube could then be taken out of the inert atmosphere chamber. The tube was optionally submerged in liquid nitrogen in order to suddenly freeze the solution. The tube was then placed in a thermostatically controlled bath at a temperature below the freezing temperature of the solvent (for example at 6° C. with DMSO) and the other side of the valve was connected to the vacuum pump. The contents of the test tube were then put under vacuum by opening the valve ($10^{-5}$ mbar). After about 15 hours (for 1 g of solution) or about 60 hours (4 to 6 g of solution), [typically one night or a weekend], a diaphanous and dry solid was observed in place of the solution (see FIG. 2). This could then be recovered by opening the test tube. Alternatively, if it was desired to keep the aerogel under an inert atmosphere, depending on what was desired to do thereto afterwards, the valve was sealed, the tube was replaced, with the sealed valve, in the controlled atmosphere glovebox and the tube was opened under an inert atmosphere.

The procedures from example 1 above, carried out starting from single-walled carbon nanotubes synthesized using the electric arc technique, were also carried out with single-walled carbon nanotubes manufactured from the HiPCO process (high-pressure carbon monoxide process), Swan nanotubes (multi-walled nanotubes with 2 to 4 walls), and multi-walled nanotubes from Arkema, with similar results.

Example 2

Measurement of the Bulk Density of the Aerogel of Example 1

Measurement of the Volume of the Aerogel:

The aerogel was prepared according to example 1 from a sodium salt of single-walled nanotubes synthesized using the electric arc technique. 4 ml of a solution of individualized reduced carbon nanotubes in DMSO were freeze dried in a test tube. A mark was made on the wall of the test tube at the level of the upper surface of the aerogel.

After having withdrawn the aerogel from the test tube, a liquid was introduced therein up to the level of the aforementioned mark. The volume of liquid was then measured in a graduated cylinder: 2.5 ml. Alternatively, the liquid could be weighed, and its volume determined from its density.

Measurement of the Mass of the Aerogel

The aerogel withdrawn from the test tube above was weighed: 6.0 mg.

Bulk Density

The bulk density of the aerogel was calculated from the mass/volume (determined above) ratio: 6.0/2.5=2.4 mg/cm³.

Example 3

Measurement of the Volume Occupied by the Pores of the Aerogel of Example 2

The density of the single-walled nanotubes being 1.4 g/cm³, a mass of 6.0 mg results in a volume $V=m/d=6.0 \times 10^{-3}/1.4=4.3 \times 10^{-3}$ cm³.

The percentage of the volume of the pores was then simply deduced as follows: $(V_{overall}-VNT)/V_{overall}$, $V_{overall}$ representing the volume of the aerogel as determined in example 2.

Thus, for the aerogel of example 2, the % of the volume of the pores was: (2.5−0.0043)/2.5=99.8%.

Example 4

Measurement of the Specific Surface Area of the Aerogel of Example 2

The measurement of the specific surface area was carried out by krypton adsorption and by the BET method.

The specific surface area determined by krypton adsorption was: 311 m²/g.

The specific surface area determined by the BET method was: 345 m²/g.

It should be understood that the two methods give an identical value.

Example 5

Measurement of the Electrical resistivity of the Aerogel of Example 1

In order to eliminate problems of contact resistances, the electrical resistivity measurements of the aerogels were carried out by the method known as the "four-point method".

Carbon nanotube aerogels were prepared according to example 1 from three different nanotube sources: nanotubes known as "Elicarb" sold by Thomas Swan, nanotubes synthesized by the electric arc method and nanotubes known as "HiPCO nanotubes".

Around a sample of cylindrical shape, four rings were formed with silver lacquer, in order to ensure good geometry of the field lines. The resistance measurements revealed a conductivity of 5.0 S/cm for an aerogel of "Elicarb" nanotubes, 0.3 S/cm for nanotubes synthesized by the electric arc method and 0.03 S/cm for "HiPCO" nanotubes.

Example 6

Preparation of a Carbon Nanotube Aerogel from a Solution of a Polyelectrolyte Salt of Carbon Nanotubes and of PMMA in DMSO A solution of individualized reduced carbon nanotubes in DMSO was prepared according to the protocol described in example 1 from "Elicarb" carbon nanotubes sold by Thomas Swan. 6% by weight (relative to the carbon nanotubes) of polymethyl methacrylate (PMMA) was added to the solution. The resulting mixture was then freeze dried according to the protocol described in example 1.

Example 7

Measurement of the Electrical Resistivity of the Aerogel of Example 6

The resistivity of the aerogel of example 6 was determined according to the protocol of example 5.

The aerogel obtained from a solution comprising PMMA and the salt of carbon nanotubes had a conductivity lower than that observed for the aerogels of example 5. In this case, an aerogel containing 6% by weight of PMMA had a conductivity of 0.05 S/cm instead of 5 S/cm.

Example 8

Demonstration of the Biocompatibility of an Aerogel of the Invention

The experimental principle consists in comparing the behavior of cells cultured in contact with an aerogel with "control" cells without aerogel (substrate favorable to cell growth, for example laboratory culture plates).

At time T0, the same amount of cells is cultured, in contact or not with the aerogel (a test sample and a control sample respectively); at times T1, T2, etc. (7 days, 14 days, etc. for example) the cell proliferation is then measured for each sample.

It is considered that the material is biocompatible and/or that there is an absence of cytotoxicity when the values obtained for the test sample are greater than or equal to 75% of the values of the control sample.

In order to quantify the cell proliferation, the MTS test (Promega's Cell Titer 96 Aqueous One Solution Cell Proliferation Assay, Promega) may be used. The principle of this test is to measure the bioreduction of the tetrazolium salt to a colored formazan product by the living cells.

The quantification can be made directly by counting the cells or indirectly by colorimetric change that expresses the modification of the substrate (optical density measurements).

LIST OF REFERENCES

[1] "*Les aérogels et le structure alvéolaires: deux exemples de mousses de carbone*" [Aerogels and the cellular structure: two examples of carbon foams] by L. Kocon and T. Piquero, in *L'actualité Chimique*, No. 245-246, pp. 119-123 (March-April 2006)

[2] "Nouveaux concepts d'élaboration de matériaux carbonés poreux" [Novel concepts in producing porous carbon materials] by C. Vix-Guterl, J. Parmentier, P. Delhaés, in *L'actualité chimique*, No. 245-246, pp. 124-128 (March-April 2006)

[3] "*Synthesis of highly ordered carbon molecular sieves via template-mediated structural transformation*" by R. Ryoo, S.-H. Soo, S. Jun, in *The Journal of Physical chemistry B*, 103 (37), pp. 7743-7746 (1999)

[4] "*High-thermal conductivity, mesophase pitch-derived carbon foams: effect of precursors on structure and properties*" by J. Klett et al. in *Carbon*, 38, pp. 153-173 (2000)

[5] "*Novel high strength graphitic foams*", by T. Beechem, K. Lafdi, in *Carbon*, 44, pp. 1548-1549 (2002)

[6] "*Fabrication of nano-structure control of carbon aero gels via microemulsion templated sol-gel polymerization method*", by D. Wu, R. Fu, M. S. Dresselhaus, G. Dresselhaus, in *Carbon*, 44, pp. 675-680 (2005)

[7] "*Preparation and properties of resorcinol formaldehyde organic and carbon gels*", by S. A. Al-Muthtsabeb, J. A. Ritter, in *Adv. Mater.*, 15(2), pp. 101-104 (2003)

[8] Schaffer, M. S. P., Windle, A. H., "Fabrication and Characterization of Carbon Nanotube/poly(vinyl alcohol) Composites", Adv. Mater., 11, pp. 937-941 (1999)

[9] "Nanotubes from carbon" by P. M. Ajayan (Chem. Rev., vol. 99, p. 1787, 1999)

[10] Aldissi, M.; Schmitz, B.; Lazaro, E.; Bhamidipati, M.; Dixon, B., "Conducting Polymers in Ultracapacitor Applications", 56. sup. th Annu. Tech. Conf.-Soc. Plast. Eng., (Vol. 2), pp. 1197-1201 (1998)

[11] An, K. H.; Kim, W. S.; Park, Y. S.; Moon, J.-M.; Bae, D. J.; Lim, S. C.; Lee, Y. S.; Lee, Y. H. "Electrochemical Properties Of High-Power Supercapacitors Using Single-Walled Carbon Nanotube Electrodes", Adv. Funct. Mater. 11, pp. 387-392 (2001)

[12] Yu, R., Chen, L., Liu, Q., Lin, J., Tan, K.-L., Ng, S. C., Chan, H. S. O., Xu, G.-Q., Hor, T. S. A. "Platinum Deposition On Carbon Nanotubes Via Chemical Modification", Chem. Mater. 10, pp. 718-722 (1998)

[13] Planeix, J. M.; Coustel, N.; Coq, B.; Brotons, V.; Kumbhar, P. S.; Dutartre, R.; Geneste, P.; Bernier, P.; Ajayan, P. M., "Application of Carbon Nanotubes As Supports_in Heterogeneous Catalysis", J. Am. Chem. Soc. 116, pp. 7935-7936 (1994)

[14] Tans, S. J., Verschueren, A. R. M., Dekker, C., "Room-Temperature Transistor Based On A Single Carbon Nanotube", Nature 393, pp. 49-52 (1998)

[15] Bachtold, A.; Hadley, P.; Nakanishi, T.; Dekker, C., "Logic Circuits With Carbon Nanotube Transistors". Science 294 pp. 1317-1320 (2001)

[16] Yodh et al., "Carbon nanotube aerogels", Advanced Materials, 2007, 19, pp. 661-664

[17] Backov et al., French Patent Application No. 06/11143 (publication No. FR 2 910 458)

[18] "Synthesis of graphite intercalation compounds", A. Hérold in Chemical physics of intercalation, A. P. Legrand and S. Flandrois Eds, NATO ASI Series, series B, Vol. 172, pp. 3-45 (1987)

[19] C. Stein, J. Poulenard, L. Bonnetain, J. Golé, C. R. Acad. Sci. Paris 260, 4503 (1965)

[20] "Synthesis of graphite intercalation compounds", A. Hérold in Chemical physics of intercalation, A. P. Legrand and S. Flandrois Eds, NATO ASI Series, series B, Vol. 172, pp. 3-45 (1987)

[21] F. Béguin and R. Setton New ternary lamellar compounds of graphite, Carbon 13, 293-295 (1975)

[22] French Patent Application No. FR 2 881 362
[23] Matyjaszewski, K.; Eds.; Advances in Controlled/Living Radical Polymerization, (American Chemical Society 2003)
[24] Hsieh, H. L.; Quirk, R. P.; Eds.; Anionic Polymerization Principles and Practical Applications, (Marcel Dekker 1996)
[25] Matyjaszewski, K.; Davies, T. P.; Eds.; Handbook of Radical Polymerization, (Wiley-Interscience 2002)
[26] Fontaine, L.; Initiation à la Chimie et à la Physico-Chimie Macromoléculaires [Introduction to macromolecular chemistry and physical chemistry] (Groupe Français d'Etudes et d'Applications des Polymères [French Group of Polymer Studies and Applications] volume 12 (Chapter 3))
[27] Chakraborty et al., "Functionalization of potassium graphite", *Angew. Chem. Int. Ed.*, 46, 4486-4488 (2007)
[28] Stankovitch et al., "Graphene based composite materials", *Nature*, 442, 282-286 (2006)
[29] FR 04/05120
[30] WO 2006/136715
[31] Matyjaszewski, K.; Eds.; Cationic Polymerizations Mechanisms, Synthesis, and Applications, (Marcel Dekker 1996)
[32] FR 2 873 381
[33] "Chemistry of Carbon Nanotubes" by Dimitrios Tasis, Nikos Tagmatarchis, Alberto Bianco and Maurizio Prato, *Chem. Rev.* 2006, 106, 1105-1136
[34] Pénicaud et al., "Spontaneous dissolution of a single-wall carbon nanotube salt", J. Am. Chem. Soc., 127, 8-9, (2005)
[35] WO 2005/073127
[36] WO 2004/076381
[37] Logo et al., "Mechanical damage of carbon nanotubes by ultrasound", *Carbon*, 34(6) 814-816, (1996)
[38] Badaire et al., "In situ measurement of nanotube dimensions in suspensions by depolarized dynamic light scattering", *Langmuir*, 20: 10367-10370 (2004)
[39] Heller et al., "Concomitant length and diameter separation of single-walled carbon nanotubes", *J. Am. Chem. Soc.*, 126: 14567-14573 (2004)
[40] Hennrich et al., "The mechanism of cavitation-induced scission of single-walled carbon nanotubes", *J. Phys. Chem. B*, 111: 1932-1937 (2007)
[41] Islam et al., "High weight fraction surfactant solubilization of single-wall carbon nanotubes in water", Nanoletters, Vol. 3(2): 269-273 (2003)

The invention claimed is:

1. A process for preparing a surfactant-free aerogel of individualized carbon nanotubes comprising the following steps carried out under an inert atmosphere:
   (a) reducing carbon nanotubes by an alkali metal in order to result in a polyelectrolyte salt of carbon nanotubes;
   (b) exposing said polyelectrolyte salt of carbon nanotubes to a solvent consisting of one or more non-aqueous surfactant-free polar aprotic solvents in order to result in a solution consisting of individualized reduced carbon nanotubes and said solvent;
   (c) freezing said solution of individualized reduced carbon nanotubes; and
   (d) sublimating the solvent, in order to form the surfactant-free aerogel of individualized carbon nanotubes.

2. The process as claimed in claim 1, in which the reducing step (a) is carried out in the presence of a nucleophilic aprotic solvent, the structure of which contains at least one oxygen atom.

3. The process as claimed in claim 2, wherein the nucleophilic aprotic solvent is tetrahydrofuran (THF).

4. The process as claimed in claim 1, wherein the alkali metal is sodium, lithium or potassium, and the polyelectrolyte salt of carbon nanotubes is a ternary compound of structure $Na(THF)_yC_x$, $Li(THF)_yC_x$ or $K(THF)_yC_x$ wherein x represents an integer between 6 and 200, and y represents an integer between 0 and 8.

5. The process as claimed in any one of claims 1 to 4, wherein the reducing step a) comprises the addition, to the carbon nanotubes, under an inert atmosphere, of an alkali metal polyaryl salt of formula $A^+B^-$, in which:
   $A^+$ represents a cation of an alkali metal ion, and
   $B^-$ represents an anion of a polyaromatic compound.

6. The process as claimed in claim 5, wherein the polyaromatic compound is selected from the group consisting of naphthalene, phenanthrene, biphenyl, anthracene, perylene, benzophenone, fluorenone, benzoquinone and anthraquinone.

7. The process as claimed in claim 1, wherein the one or more polar aprotic solvents of step (b) are selected from the group consisting of is sulfolane, dimethyl sulfoxide, dimethylformamide, N-methylpyrrolidone, N-methylformamide, and combinations thereof.

8. The process as claimed in claim 1, wherein the nanotubes used in step (a) are single-walled or multi-walled carbon nanotubes.

9. The process as claimed in claim 1, wherein the freezing step (c) is carried out slowly by immersing the solution of individualized carbon nanotubes in a thermostatically-controlled medium at a temperature below the freezing temperature of the one or more polar aprotic solvents used in step (b), or else suddenly by immersing the solution of individualized carbon nanotubes in liquid nitrogen.

10. The process as claimed in claim 9, wherein the polar aprotic solvent used in step (b) is dimethyl sulfoxide (DMSO) and the sublimating step (d) is carried out by thermostatically controlling the solution of carbon nanotubes in the DMSO at a temperature below 18° C.

11. The process as claimed in claim 1, wherein the aerogel has a bulk density of between 0.1 and 5 $mg/cm^3$.

12. The process as claimed in claim 1, wherein the aerogel has a pore volume that is at least 99% of the total volume of the aerogel.

* * * * *